(12) United States Patent
DePetrillo (10) Patent No.: US 6,374,675 B1
(45) Date of Patent: Apr. 23, 2002

(54) ACOUSTIC MICROSCOPY DIE CRACK INSPECTION FOR PLASTIC ENCAPSULATED INTEGRATED CIRCUITS

(75) Inventor: Kevin Michael DePetrillo, San Jose, CA (US)

(73) Assignee: Advanced Micro Devices, Inc,, Sunnyvale, CA (US)

( * ) Notice: Subject to any disclaimer, the term of this patent is extended or adjusted under 35 U.S.C. 154(b) by 0 days.

(21) Appl. No.: 09/531,426

(22) Filed: Mar. 20, 2000

(51) Int. Cl.[7] .............................................. G01N 29/00
(52) U.S. Cl. .............................. 73/610; 73/600; 73/606; 73/618; 73/629
(58) Field of Search .......................... 73/600, 610, 606, 73/620, 629, 579, 582, 587, 596, 618, 619, 627, 646, 588, 599; 250/559.45, 307, 234

(56) References Cited

U.S. PATENT DOCUMENTS

| | | | | | |
|---|---|---|---|---|---|
| 4,432,235 | A | * | 2/1984 | Renzel et al. | 73/611 |
| 4,980,865 | A | * | 12/1990 | Ishibashi et al. | 73/607 |
| 5,505,090 | A | * | 4/1996 | Webster | 73/657 |
| 5,627,320 | A | * | 5/1997 | Moore | 73/606 |
| 5,631,425 | A | * | 5/1997 | Wang et al. | 73/606 |
| 5,641,906 | A | * | 6/1997 | Moore | 73/614 |
| 5,977,555 | A | * | 11/1999 | O'Dwyer | 250/559.45 |
| 6,089,095 | A | * | 7/2000 | Yang et al. | 73/579 |

* cited by examiner

*Primary Examiner*—Hezron Williams
*Assistant Examiner*—Jacques M. Saint-Surin

(57) ABSTRACT

A novel method of non-destructive die crack inspection of a plastic encapsulated integrated circuit (PEIC) uses a scanning acoustic microscope, such as a C-mode scanning acoustic microscope. To generate scan of a die surface of the PEIC, the width of a data gate of the microscope is set to scan only the die surface. Then, the data gate is moved to cover only die subsurface reflection area on a screen of the microscope, and scan of the die subsurface is generated.

7 Claims, 9 Drawing Sheets

Types of die cracking

Vertical Cracks

Horizontal Cracks

Slanting Corner Cracks

FIG. 3

Common Plastic Package Cracks

Typical Die Surface Crack

Typical Die Subsurface Crack

ACOUSTIC MICROSCOPY DIE CRACK INSPECTION FOR PLASTIC ENCAPSULATED INTEGRATED CIRCUITS

FIELD OF THE INVENTION

The present invention relates to integrated circuit packaging, and more particularly, to inspection performed to detect die cracks in plastic encapsulated integrated circuits.

BACKGROUND ART

In general, a plastic encapsulated integrated circuit (PEIC) consists of a silicon chip, a metal support or leadframe, wires that electrically attach the chip circuits to the leadframe and thus to the external leads, and a plastic epoxy encapsulating material to protect the chip and the wire interconnects. The leadframe is made of a copper alloy, Alloy 42 (42Ni/58Fe) or Alloy 50 (50Ni/50Fe), and is plated with gold and silver or palladium, either completely or in selected areas over nickel or nickel/cobalt. The silicon chip is usually mounted to the leadframe with an organic conductive formulation of epoxy. Wires, generally of gold but also of aluminum or copper, are bonded to the aluminum bonding pads on the chips and to the fingers of the leadframe. The assembly is then typically transfer-molded in epoxy. Following the molding operations, the external pins are plated with a lead-tin alloy, cut away from the strip, and formed.

Plastic packages are either premolded or postmolded. In the former, a plastic base is molded, the chip is then placed on it and connected to an input/output fanout pattern with wire. The die and wirebonds are usually protected by an epoxy-attached lead, which forms a cavity. Premolded packages are most often used for high-pin-count devices or pin-grid arrays that are not amenable to flat leadframes and simple fanout patterns.

Figure 1:
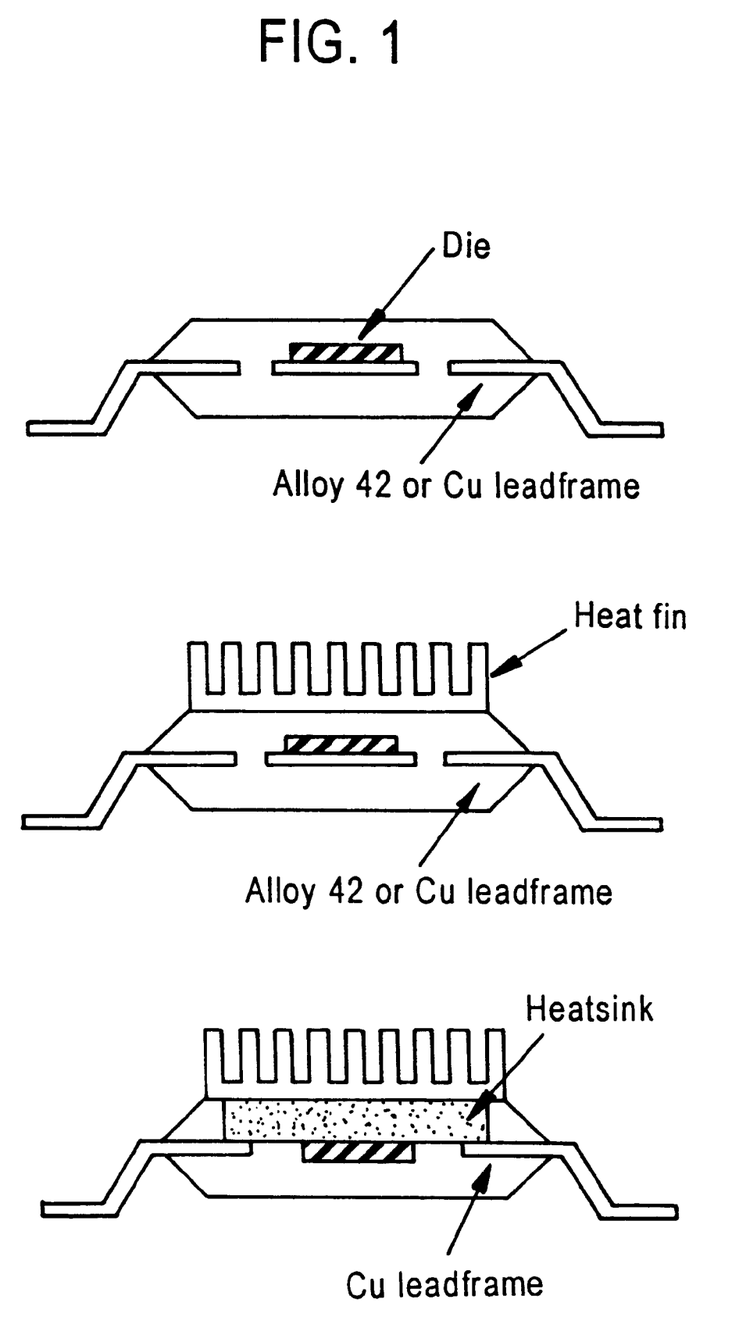
FIG. 1 illustrates various plastic encapsulated package configurations.

In the postmolded packages, the die is attached to a leadframe, which is then loaded into a multicavity molding tool and encapsulated in a thermoset molding compound via the transfer molding process. Postmolded packages are less expensive than premolded ones because are fewer parts and assembly steps. In the 1990s, about 90% of plastic packages were made using postmolding techniques. FIG. 1 illustrates various plastic package configurations having a die, an Alloy 42 or Cu leadframe, a heat fin and a heatsink.

Advantages of plastic packages over their ceramic counterparts include smaller form factors, lighter weight, better performance, and lower costs. The reliability of plastic packages has also increased substantially with improvements in encapsulants, die passivation, metallization technology, and assembly automation. However, during thermal processing, die scribing, dicing processes, or application of mechanical forces, die surface scratching and cracking may occur.

The location of a surface crack is critical, as a die surface crack across the device will cause electronic failures. Cracking can start as early as wafer fabrication. Lapping, which reduces sawing-introduced damage and thickness variations by obtaining a better degree of uniformity, induces crack growth. Also, stress imposed upon the crystal during cooling can cause cracking in the wafer. If no dislocation sources are present, the crystal will be highly stressed and can crack upon cooling.

Figure 2:
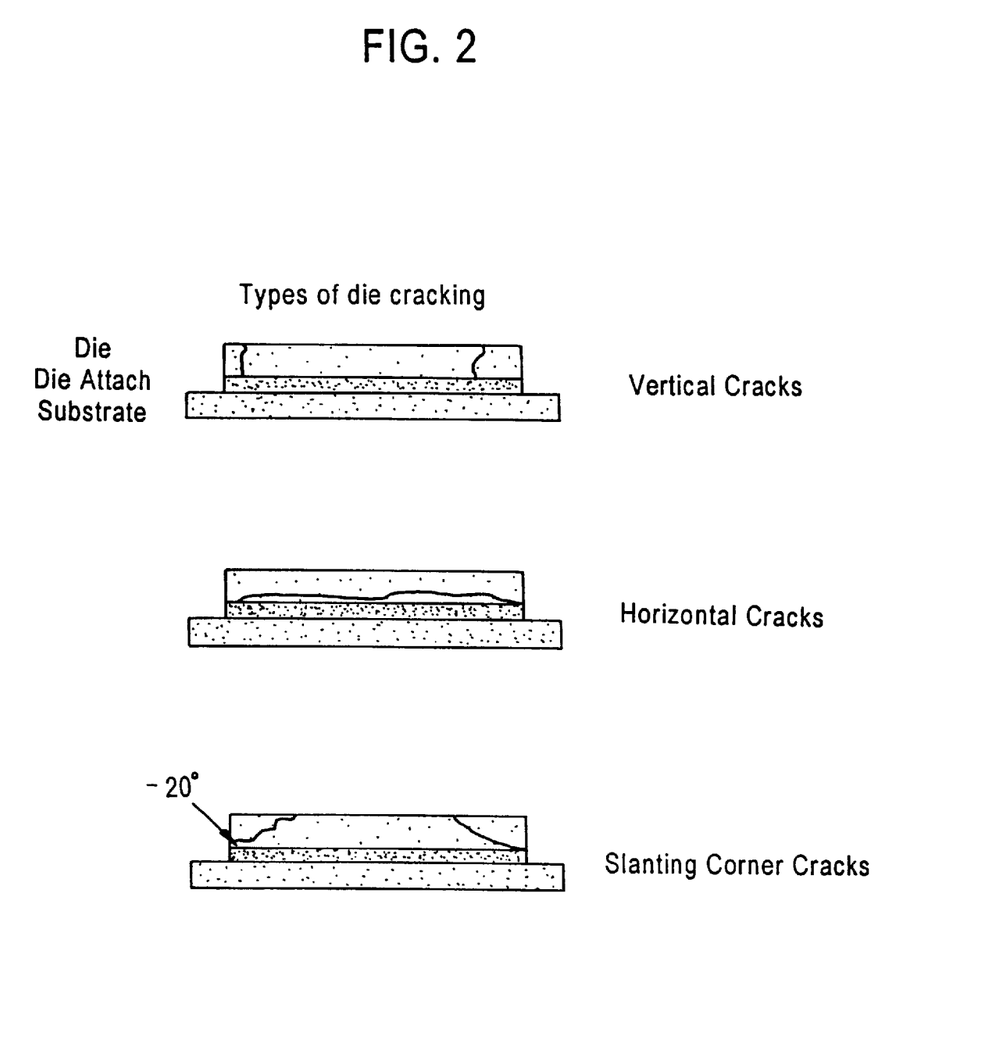
FIG. 2 shows various types of die cracks.

A major cause of die cracking is the presence of voids. Cracks often occur at the corner of the die and initiate at an edge void. Also, rigid attachments cause the die to fracture during thermal cycling. FIG. 2 illustrates such types of die cracks as vertical cracks, horizontal cracks and slanting corner cracks.

Figure 3:
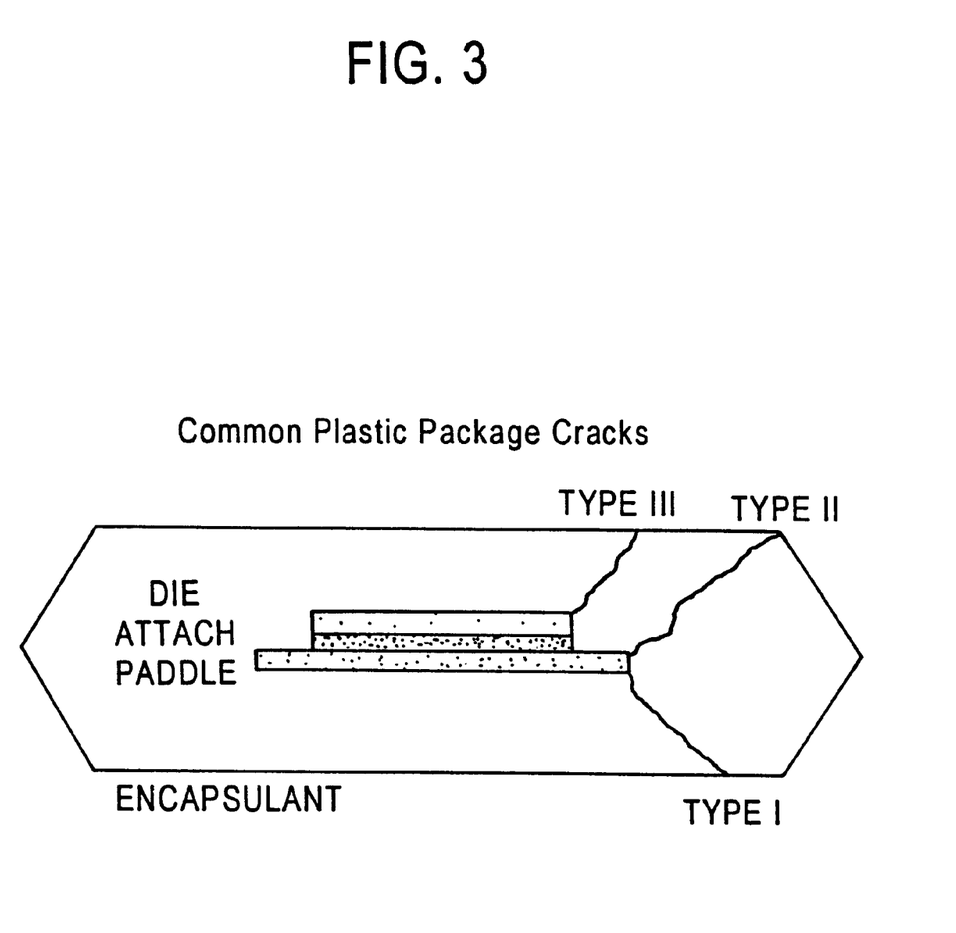
FIG. 3 illustrates common plastic package cracks.

In addition, plastic package cracks may form at delaminations at encapsulant interfaces with the die or the leadframe. The likelihood of the formation of plastic package cracks is directly proportional to the ratio of the die-paddle area to the minimum plastic case thickness. As illustrated in FIG. 3, plastic package cracks usually fall into one of three categories: I) the crack starts at the die paddle edge or corner and propagates to the bottom of the package; II) the crack starts at the die paddle edge or corner and propagates to the top of the package; III) the crack starts at the die edge or corner and propagates to the top of the package.

Current methods of crack inspection for plastic encapsulated integrated circuits require destructive techniques such as chemical decapsulation of the plastic package. Therefore, it would be desirable to create a non-destructive crack inspection technique to monitor assembly of plastic encapsulated integrated circuits. The non-destructive analysis would allow quicker crack inspection of large size samples. Also, non-destructive crack inspection would give information on the crack starting region and its propagation.

SUMMARY OF THE INVENTION

The present invention offers a novel method of non-destructive die crack inspection of a plastic encapsulated integrated circuit (PEIC). The method involves placing the PEIC in a sample chamber of a scanning acoustic microscope, such as a C-mode scanning acoustic microscope. To generate scan of a die surface of the PEIC, the width of a data gate of the microscope is set to scan only the die surface of the PEIC.

Further, the data gate may be moved to cover only die subsurface reflection area on a screen of the microscope, and scan of the die subsurface is generated.

In a preferred embodiment of the invention, the scan of the die surface is performed with the same resolution as the scan of the die subsurface.

Still other objects and advantages of the present invention will become readily apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

DESCRIPTION OF THE INVENTION

As discussed above, conventional methods of crack inspection for plastic encapsulated integrated circuits require destructive techniques such as chemical decapsulation of the plastic package. In accordance with the present invention, a non-destructive die crack inspection of plastic encapsulated integrated circuits is performed using Scanning Acoustic Microscopy.

Figure 4:
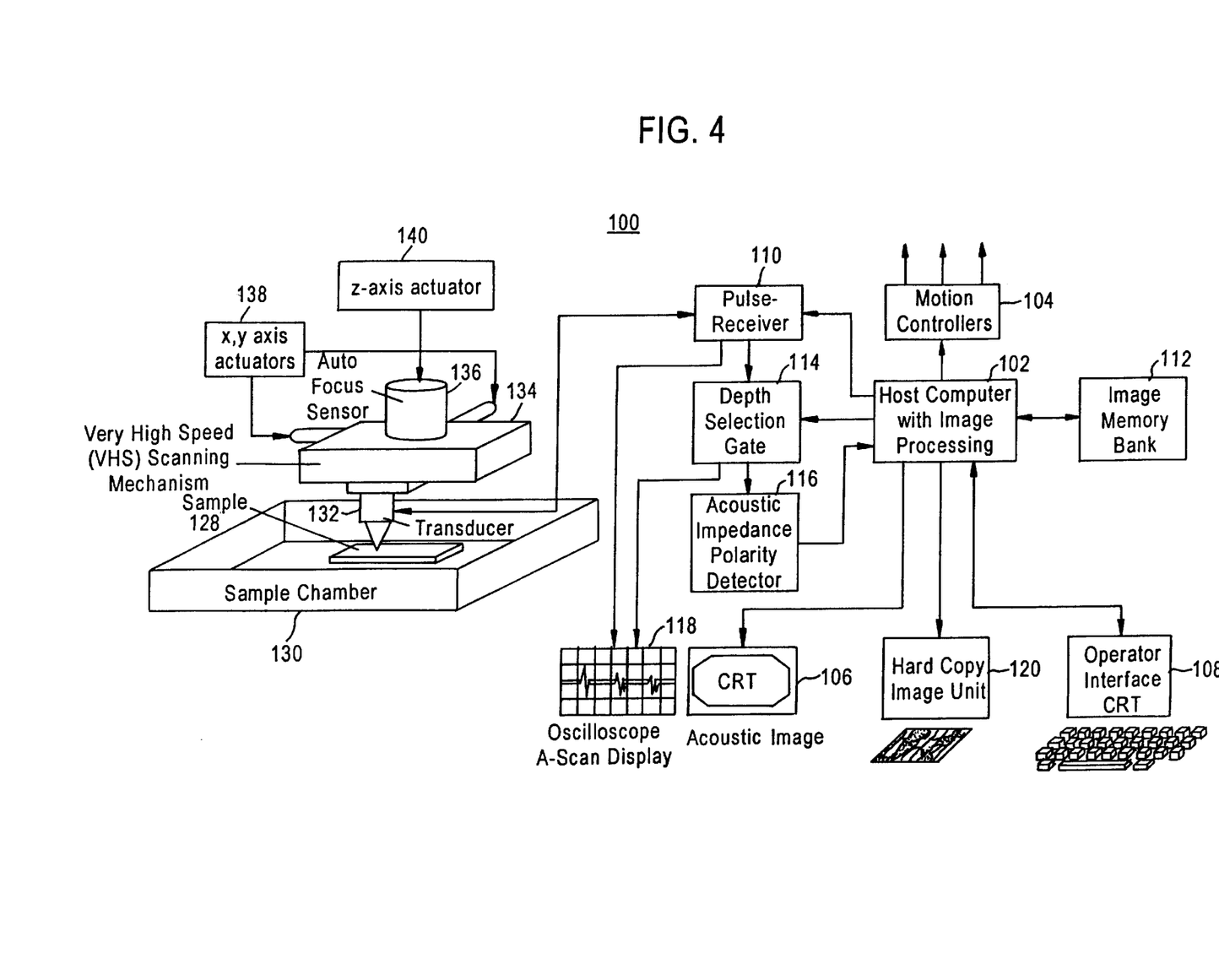
FIG. 4 shows an exemplary block diagram of a C-mode scanning acoustic microscope that may be used in the present invention.

FIG. 4 shows an exemplary block diagram of a C-Mode Scanning Acoustic Microscope (SAM) 100 that may be used for performing die crack inspection in accordance with the present invention. The SAM 100 comprises a host computer 102 with image processing capabilities. The host computer 102 may interact with motion controllers 104, acoustic image CRT 106, operator interface CRT 108, pulse receiver 110, image memory bank 112, depth selection gate 114, acoustic impedance polarity detector 116, oscilloscope 118 for display of returning waves (A-Scan), and hard copy image unit 120.

A plastic encapsulated integrated circuit (sample) 128 to be inspected is fixed in a sample chamber 130. A transducer 132 for generating ultrasound waves is carried by a very high speed (VHS) mechanical scanner 134 so as to move a single spot of ultrasound waves across the sample. The transducer 132 may be an acoustic lens assembly for generating acoustic waves ranging from 10 to 100 MHz. An auto focus sensor 136 focuses the spot produced by the transducer 132 on the sample. The motion controllers 104 controls X-, Y-axis actuators 138 to move the VHS scanner 134 with respect to the sample chamber 130. Also, the motion controllers 104 drives a Z-axis actuator 140 to control the auto focus sensor 136.

The SAM 100 allows the user to select the depth of the scan by focusing the spot of acoustic waves on a required area of interest. The echoes arising from that area are electronically gated by the depth selection gate 114 for display by the A-scan oscilloscope 118. The waveform displayed by the oscilloscope 118 contains a data gate, which is the primary source of information for the C-mode image. The acoustic signal within the data gate is used for obtaining the peak amplitude image as well as the phase inversion data. The depth selection gate 114 enables the user to adjust the width of the data gate. The polarity detector 116 determines the polarity of the acoustic impedance signal so as to enable the CRT display 106 to display an enhanced acoustic image having both amplitude and polarity information.

Figure 5:
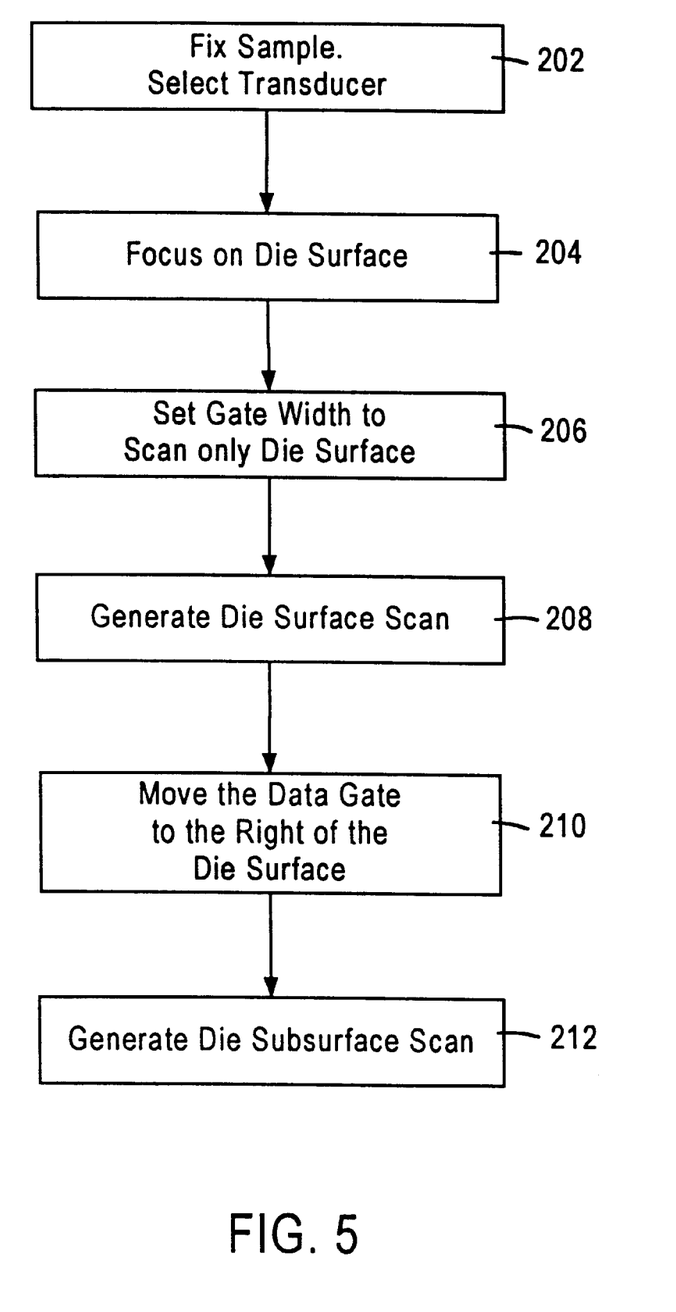
FIG. 5 shows a flow chart of a die crack inspection method of the present invention.

FIG. 5 shows a flow-chart illustrating a method of die crack inspection in accordance with the present invention. A plastic encapsulated integrated circuit package 128 is fixed in the sample chamber 130, and the transducer 132 is selected based on package type (block 202). The transducer is focused on the surface of the die in the package 128 (block 204).

Figure 6:
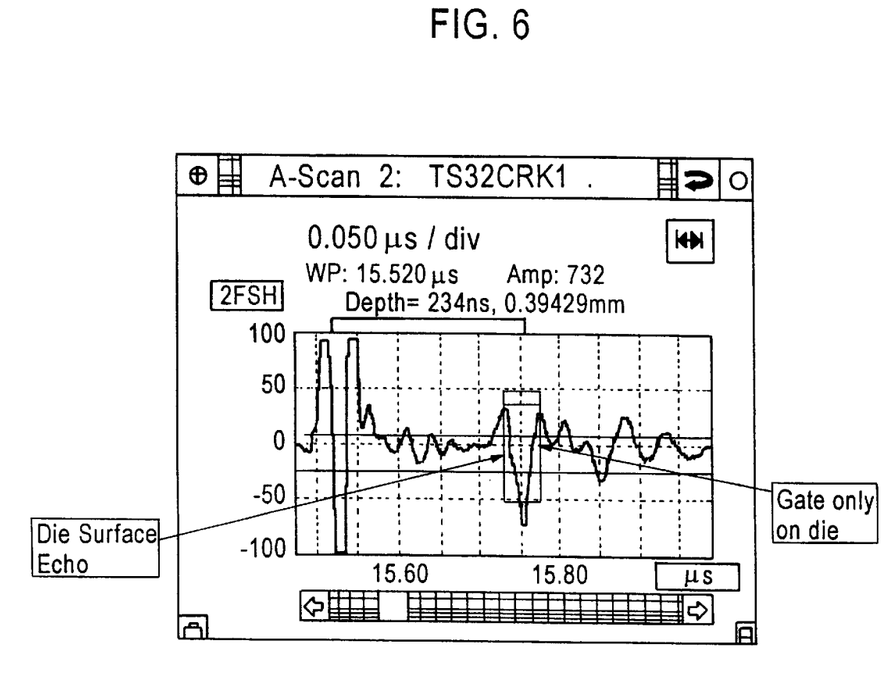
FIG. 6 illustrates setting gate width to perform a die surface scan.
Figure 7:
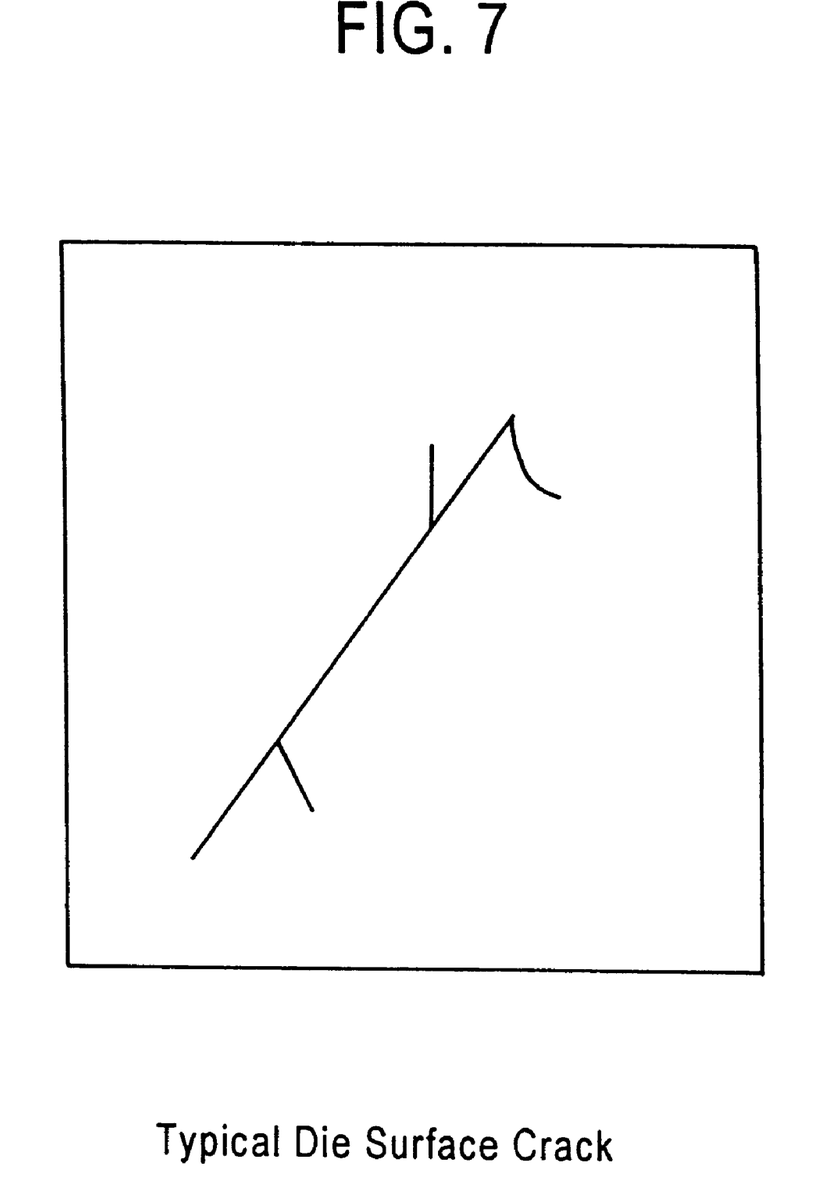
FIG. 7 represents an acoustic image produced as a result of the die surface scan.

As illustrated in FIG. 6 showing the acoustic signal displayed by the A-scan display 118, the width of the data gate is set to scan only the die surface (block 206). Then, scan of the die surface is generated using high resolution, e.g. 700 to 900 data points (block 208). The acoustic image displayed on the CRT display 106 is checked for cracks at the die surface. The cracks may appear as black lines with some small delaminations in the same area. Most cracks appear with no delamination and are a result of some type of mechanical stress to the package. FIG. 7 illustrates the acoustic image of a typical die surface having cracks.

Figure 8:
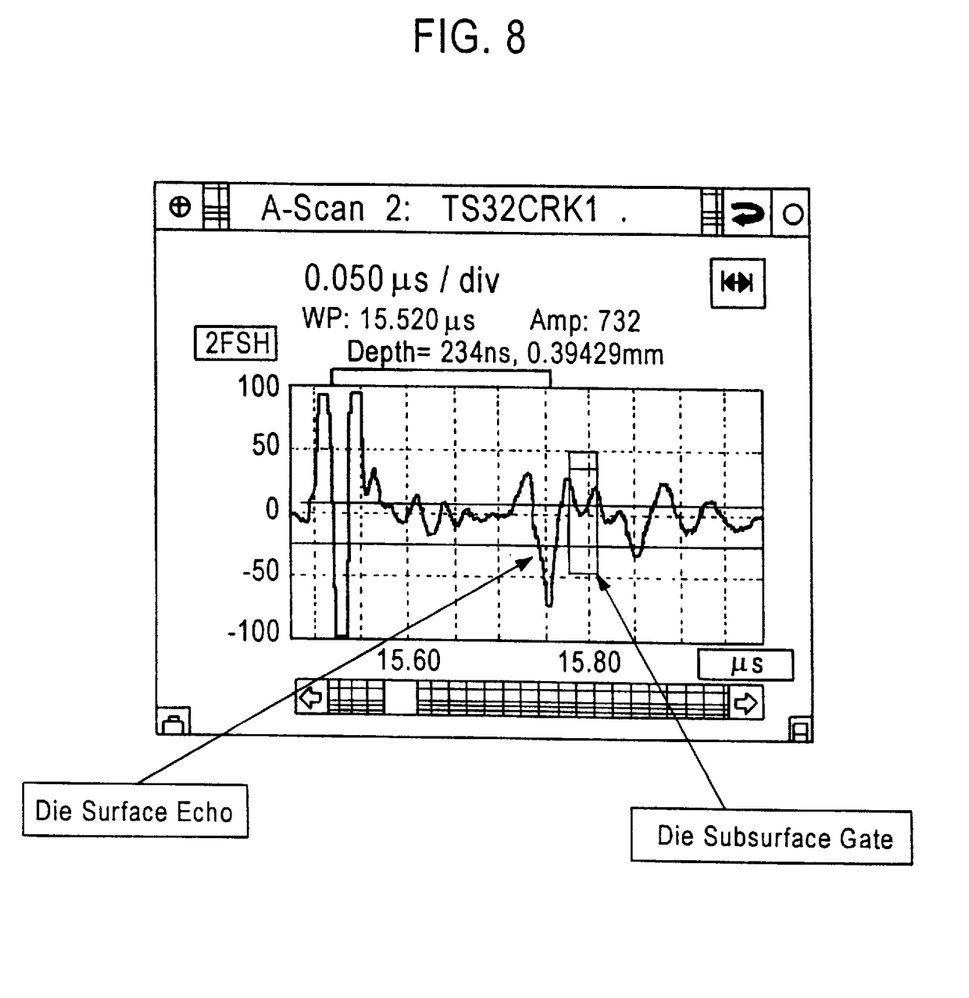
FIG. 8 illustrates setting a data gate to perform a die subsurface scan.
Figure 9:
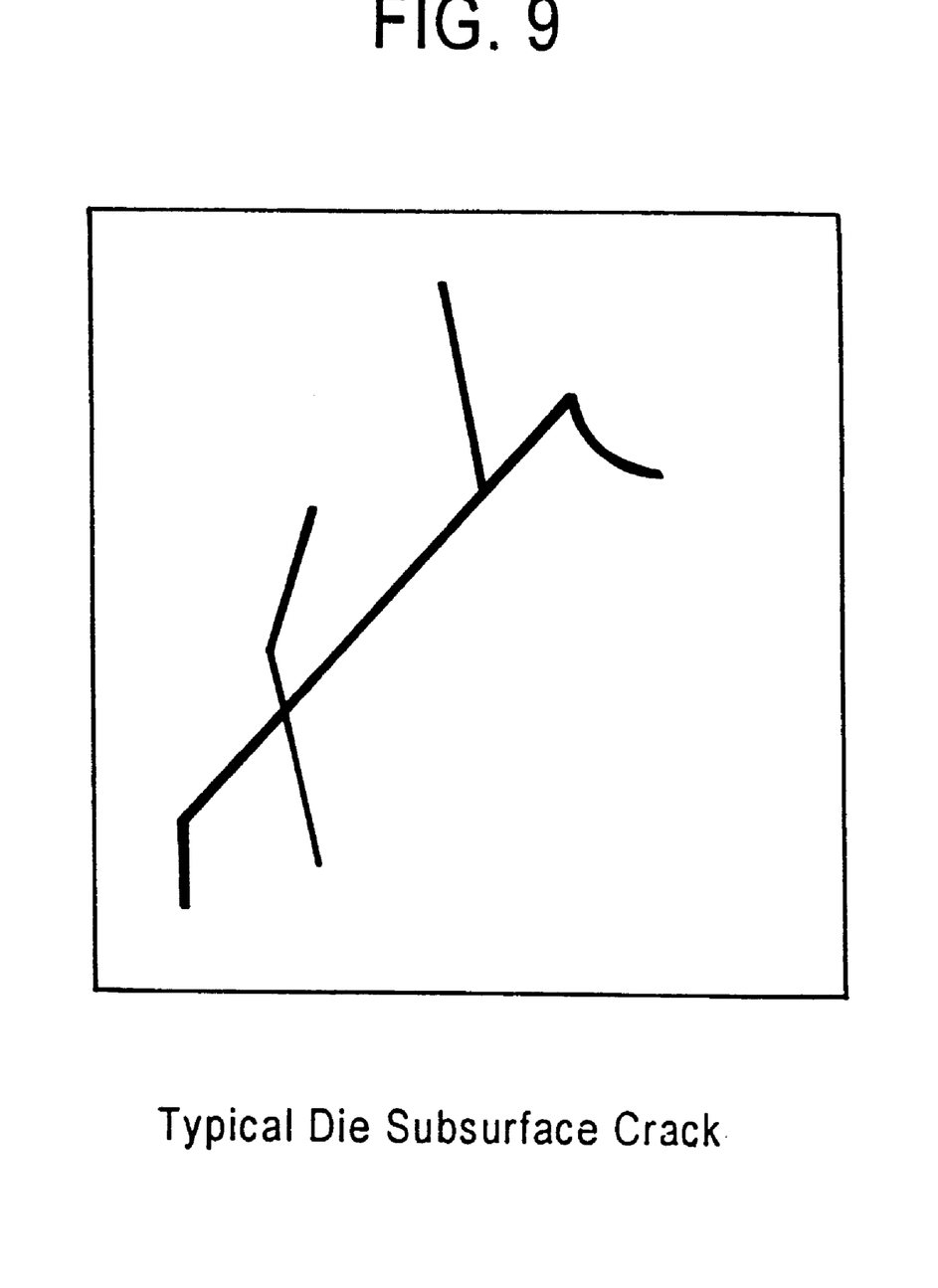
FIG. 9 represents an acoustic image produced as a result of the die subsurface scan.

Then, step 210 is carried out to move the data gate from the die surface to the die subsurface reflection area (FIG. 8). The area on the waveform displayed by the A-scan display 118 between a die and the top of the paddle, to which the die is attached, represents the die subsurface reflection. The width of the data gate is selected to cover only the area of the die subsurface reflection. Thereafter, the SAM 100 generates scan of the die subsurface, which is an area of the package 128 causing the die subsurface reflection on the screen of the A-scan display 118 (block 212). The die subsurface scan is generated with the same resolution as the scan of the die surface. FIG. 9 shows the acoustic image representing the die subsurface scan.

A die crack may be recognized by identifying a dark area on the die. If there is a laser mark on the package, it may have to be removed to see the cracks. The subsurface scan can be used to detect crack branches that may not appear during the die surface scan. This information is helpful in determining how the die was cracked and where the crack may have started. A crack at some portions of the die surface may be undetectable until a subsurface scan is performed. For example, cracks that start at the bottom of the die and do not break the die surface completely can be hard to see without the die subsurface scan.

Thus, in accordance with the present invention, die crack inspection of a plastic encapsulated integrated circuit is performed using acoustic microscopy. A die surface scan is followed by a die subsurface scan to increase the accuracy of crack detection.

In this disclosure, there are shown and described only the preferred embodiment of the invention, but it is to be understood that the invention is capable of changes and modifications within the scope of the inventive concept as expressed herein.

What is claimed is:

1. A method of non-destructive crack inspection of a plastic encapsulated integrated circuit (PEIC), the method comprising the steps of:

placing the PEIC in a sample chamber of a scanning acoustic microscope, setting width of a data gate of the microscope to scan only a surface of a die in the PEIC, and generating scan of the die surface to detect cracks on the surface of the die.

2. The method of claim 1, further comprising the steps of:

setting the data gate to cover only a die subsurface reflection area on a screen of the microscope, and generating scan of a die subsurface to detect cracks in the die undetectable during the scan of the die surface.

3. The method of claim 2, wherein the scan of the die surface is performed with the same resolution as the scan of the die subsurface.

4. The method of claim 2, wherein if the die subsurface has cracks, an image of the die subsurface having the cracks is produced after the step of generating the scan of the die subsurface, to provide visual die crack inspection.

5. The method of claim 1, wherein the scan of the die surface is performed using resolution in the range from 700 to 900 data points.

6. The method of claim 1, wherein a C-mode scanning acoustic microscope is used for die crack inspection.

7. The method of claim 1, wherein if the die surface has cracks, an image of the die surface having the cracks is produced after the step of generating the scan of the die surface, to provide visual die crack inspection.

\* \* \* \* \*